(12) United States Patent
Nakayama et al.

(10) Patent No.: US 8,445,427 B2
(45) Date of Patent: May 21, 2013

(54) ENDOTOXIN ADSORBENT, AND METHOD FOR REMOVING ENDOTOXIN USING THE SAME

(75) Inventors: Minoru Nakayama, Minamata (JP); Masami Todokoro, Tokyo (JP)

(73) Assignee: JNC Corporation, Tokyo (JP)

( * ) Notice: Subject to any disclaimer, the term of this patent is extended or adjusted under 35 U.S.C. 154(b) by 311 days.

(21) Appl. No.: 11/603,083

(22) Filed: Nov. 22, 2006

(65) Prior Publication Data

US 2007/0213258 A1    Sep. 13, 2007

(30) Foreign Application Priority Data

Nov. 25, 2005   (JP) ................................. 2005-340538

(51) Int. Cl.
- *A61K 38/00* (2006.01)
- *A61K 31/00* (2006.01)
- *A61K 47/00* (2006.01)
- *A01N 25/00* (2006.01)

(52) U.S. Cl.
USPC ........................................... 514/2.1; 514/777

(58) Field of Classification Search ........................ None
See application file for complete search history.

(56) References Cited

U.S. PATENT DOCUMENTS

| | | | | |
|---|---|---|---|---|
| 4,090,919 A | * | 5/1978 | Chibata et al. | 435/178 |
| 4,576,928 A | * | 3/1986 | Tani et al. | 502/404 |
| 5,747,320 A | * | 5/1998 | Saha et al. | 435/209 |
| 6,699,386 B2 | * | 3/2004 | Todokoro et al. | 210/198.2 |
| 2002/0130082 A1 | | 9/2002 | Todokoro et al. | |

FOREIGN PATENT DOCUMENTS

| | | |
|---|---|---|
| EP | 0362879 A1 | 11/1990 |
| JP | 01-127039 | 5/1989 |
| JP | 06-16843 B | 3/1994 |
| JP | 2001-276611 | 10/2001 |
| JP | 2002-263486 A | 9/2002 |
| JP | 2004-292357 | 10/2004 |

OTHER PUBLICATIONS

Danielson et al. Glycoconjugate J (1986) 3:363-377.*
Merchant et al. Biochem. J. (1985) 229, 369-377.*
JP 06-016843 B, 1994, machine translation.*
English translation of Office Action [dated Jul. 26, 2011] from JPO for Japanese application [JP2005-340538] corresponding to US application.
Hirayama et al., Preparation of poly(e-lysine) adsorbents and application to selective removal of lipopolysaccharides, Journal of Chromatography B, 1999, 721, pp. 187-195.

* cited by examiner

*Primary Examiner* — Layla Bland
(74) *Attorney, Agent, or Firm* — Hogan Lovells US LLP

(57) ABSTRACT

The invention provides a method for selecting and eliminating endotoxin selectively from a solution where a highly acidic substance such as heparin co-exists, and an adsorbent used therefore. The invention also provides a method for providing the endotoxin adsorbent, which includes partially modifying amino groups contained within an amino group-containing molecule used as a ligand of the endotoxin adsorbent, with a molecule that is capable of reacting with an amino group.

9 Claims, 1 Drawing Sheet

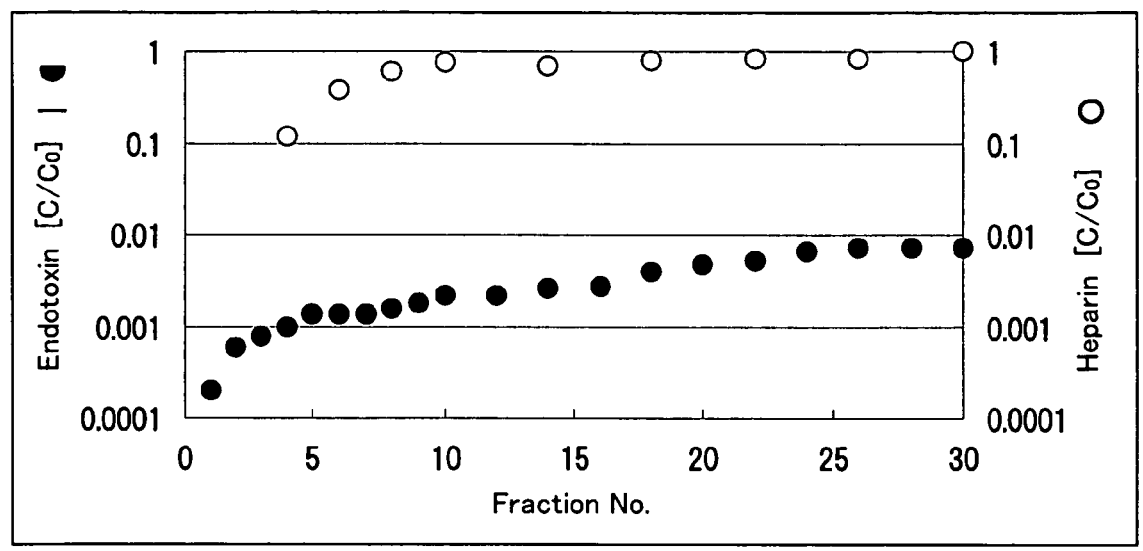

ENDOTOXIN ADSORBENT, AND METHOD FOR REMOVING ENDOTOXIN USING THE SAME

RELATED APPLICATION

This application claims benefit of priority under 35 U.S.C §119 to Japanese Patent Application No. 2005-340538 filed Nov. 25, 2005, which is herein incorporated by reference in its entirety.

TECHNICAL FIELD

The invention relates to an endotoxin adsorbent and a method for removing endotoxin using the same. More specifically, the invention relates to a method for selectively adsorbing endotoxin from a solution in which a substance showing a high acidity, such as heparin, co-exists.

BACKGROUND ART

An endotoxin is a toxic substance present in the bacterial body component of a bacteria, and released when a bacteria is killed. A structural component of endotoxin is lipopolysaccharide, which is produced inside the bacterial body by a bacteria living during the production process of a medicinal drug product, and contaminates the medicinal drug product when it is killed. Adsorbents by activated charcoal or ion-exchanger, filtration methods using membranes, membrane filters or the like, decomposition methods using high temperature/high pressure treatments or acid or alkali, are known methods for removing endotoxin. All the methods have merits and demerits, posing problems for industrial use. For instance, removal of endotoxin in medicinal drug product manufacturing sometimes cannot be carried out under harsh conditions from the point of maintaining the stability of the original medicinal drug product, or due to the tiny amounts of endotoxin present, although adsorption is carried out successfully in a laboratory, the adsorption cannot be carried out satisfactorily in an actual industrial scale, or the medicinal drug product itself is adsorbed onto the adsorbent, such that it is by no means satisfactory. In contrast, a number of adsorbents have been disclosed in recent years, in order to allow endotoxin adsorption to be also satisfactory for the industry. For instance, an adsorbent constituted from a poly-amino acid containing a modified group having a fatty series group and/or an aryl at the extremity of a side chain and/or a main chain has been disclosed (Japanese Patent Publication No. H6-16843), and an adsorbent comprising a poly-amino acid spherical particle serving as a carrier and a imidazole derivative conjugated thereto has been disclosed (Japanese Patent Application Laid-open No. H1-127039). In addition, a method whereby a basic substance is immobilized and the pore size of the adsorbent is controlled to adsorb endotoxin selectively has been disclosed (Japanese Patent Application Laid-open No. 2002-263486).

SUMMARY OF THE INVENTION

The above-described adsorbents have a problem that when highly acidic substances, such as heparin or the like, coexist, the adsorbents adsorb heparin. Consequently, the amount of adsorbed endotoxin decreases remarkably. In particular, because heparin is a substance that is used widely as blood anticoagulant, a method for selectively adsorbing endotoxin from heparin-containing blood, and the like, is desired.

It has been observed that partially modifying amino groups contained in the amino group-containing molecule used as a ligand makes endotoxins to be adsorbed and eliminated selectively from a solution where an acidic substance such as heparin co-exists. In particularly, the invention provides a method for selecting and eliminating endotoxin selectively from a solution where a highly acidic substance such as heparin co-exists, and an adsorbent used therefor.

The invention provides the following endotoxin adsorbent, method for adsorbing and removing endotoxin, and the like:

(1) An endotoxin adsorbent that includes a ligand in which amino groups present within a molecule of an amino group-containing molecule have been partially modified by a molecule that is capable of reacting with an amino group.

(2) The endotoxin adsorbent according to item (1) above, wherein the ligand is immobilized on a carrier.

(3) The endotoxin adsorbent according to item (2) above, wherein the carrier is polysaccharides or derivatives thereof.

(4) The endotoxin adsorbent according to item (3) above, wherein the polysaccharides are cellulose, agarose, dextran, chitin or chitosan.

(5) The endotoxin adsorbent according to any of items (2) to (4) above, wherein the shape of the carrier is spherical, membranous, granular or fibrous.

(6) The endotoxin adsorbent according to item (5) above, wherein the carrier is spherical cellulose, spherical sepharose or spherical dextran.

(7) The endotoxin adsorbent according to any of items (1) to (6) above, wherein the amino group-containing molecule is polylysine.

(8) The endotoxin adsorbent according to any of items (1) to (6) above, wherein the amino group-containing molecule is polyethylene imine or polyallyl amine.

(9) The endotoxin adsorbent according to any of items (1) to (8) above, wherein the molecule that is capable of reacting with an amino group is a molecule that is capable of forming an amine bond or an amide bond with an amino group.

(10) The endotoxin adsorbent according to item (9) above, wherein the molecule that is capable of forming an amine bond or an amide bond with an amino group is at least one species chosen from carboxylic acid, epoxy compound and aldehyde.

(11) The endotoxin adsorbent according to item (9) above, wherein the molecule that is capable of forming an amine bond or an amide bond with an amino group is at least one species chosen from acetic anhydride, butylglycidyl ether and phenylglycidyl ether.

(12) The endotoxin adsorbent according to any of items (1) to (11) above, wherein the molecule that is capable of reacting with an amino group forms an amine bond or an amide bond with the intramolecular amino groups of the amino group-containing molecule.

(13) The endotoxin adsorbent according to any of items (1) to (12) above, wherein the ratio of modification of amino groups of the amino group-containing molecule is 20 to 60%.

(14) An endotoxin adsorbent, wherein a ligand, which is a polylysine in which amino groups have been partially modified by a molecule that is capable of forming an amine bond or an amide bond with an amino group, is immobilized on a carrier.

(15) The endotoxin adsorbent according to item (14) above, wherein the polylysine is epsilon-polylysine.

(16) The endotoxin adsorbent according to items (14) or (15) above, wherein the carrier is polysaccharides or derivatives thereof.

(17) The endotoxin adsorbent according to item (16) above, wherein the polysaccharides are cellulose, agarose, dextran, chitin or chitosan.

(18) The endotoxin adsorbent according to any of items (14) to (17) above, wherein the shape of the carrier is spherical, membranous, granular or fibrous.

(19) The endotoxin adsorbent according to item (18) above, wherein the carrier is spherical cellulose, spherical sepharose or spherical dextran.

(20) The endotoxin adsorbent according to any of items (14) to (19) above, wherein the molecule that is capable of forming an amine bond or an amide bond with an amino group is at least one species chosen from carboxylic acid, epoxy compound and aldehyde.

(21) The endotoxin adsorbent according to any of items (14) to (19) above, wherein the molecule that is capable of forming an amine bond or an amide bond with an amino group is at least one species chosen from acetic anhydride, butylglycidyl ether and phenylglycidyl ether.

(22) The endotoxin adsorbent according to any of items (14) to (21) above, wherein the ratio of modification of amino groups of said polylysine is from 20 to 60%.

(23) A method for adsorbing and removing endotoxin by bringing the endotoxin adsorbent according to any of items (1) to (22) above in contact with an endotoxin-containing solution.

(24) A method for selectively adsorbing and removing endotoxin by bringing the endotoxin adsorbent according to any of items (1) to (22) above in contact with an endotoxin-containing solution containing heparin.

(25) The method according to items (23) or (24) above, wherein the contact of the endotoxin adsorbent with the endotoxin-containing solution is carried out using a column filled with the endotoxin adsorbent.

(26) A method for preparing the endotoxin adsorbent according to any of items (1) to (22) above, further including the step of reacting and partially modifying the amino groups present within a molecule of the amino group-containing molecule with a molecule that is capable of reacting with an amino group.

(27) A method for preparing the endotoxin adsorbent according to any of items (14) to (22) above, further including the step of immobilizing polylysine without modified amino groups onto a carrier, then, reacting amino groups of the polylysine with a molecule that is capable of forming an amino bond or an amide bond with an amino group.

According to the invention, a method for adsorbing and removing endotoxin selectively from a solution where a highly acidic substance such as heparin and the like co-exists, and an adsorbent used therefor, can be provided. In addition, according to the invention, endotoxin can be adsorbed and removed selectively from a solution (for instance, medicinal drug product, blood, blood plasma component and the like) containing a highly acidic substance such as heparin.

BRIEF DESCRIPTION OF THE DRAWINGS

The accompanying drawing, which is included to provide further understanding of the invention and is incorporated in and constitutes a part of this specification, illustrates an embodiment of the invention and together with the description serve to explain the principles of the invention. In the drawing:

FIG. 1 is a graph showing that endotoxin is more selectively removed than heparin in the endotoxin removal from heparin-containing buffer solution by the column method.

DETAILED DESCRIPTION OF THE PREFERRED EMBODIMENTS

Hereinafter, the endotoxin adsorbent of the invention and the method for adsorbing and removing endotoxin using the same will be described in detail.

First, terms used in the specification will be explained. "Partially modifying amino groups present within a molecule of an amino group-containing molecule with a molecule that is capable of reacting with an amino group" means to modify a portion of a plurality of amino groups present within a molecule of an amino group-containing molecule by reacting with a molecule that is capable of reacting with an amino group. "Highly acidic substance" means an acidic substance adsorbed by an amino group-containing molecule, decreasing the amount of adsorption of endotoxin when an endotoxin-containing solution is brought into contact with an amino group-containing molecule (for instance, epsilon-polylysine and the like) under the co-existence of such a substance.

Hereinafter, embodiments of the invention will be explained.

1. Endotoxin Adsorbent

The first embodiment of the invention relates to an endotoxin adsorbent containing a ligand wherein amino groups present within a molecule of an amino group-containing molecule have been partially modified by a molecule that is capable of reacting with an amino group.

As amino group-containing molecules used in the invention, peptides that include basic amino acids such as lysine, arginine, histidine, tryptophan, ornithine, 2,4 diaminobutyric acid and 2,3 diaminopropionic acid, or basic proteins such as protamine, polymers comprising basic amino acids such as polylysine (for instance, epsilon-polylysine and alpha-polylysine), polyhistidine, polyarginine, polytryptophan, polyornithine, poly-2,4-diaminobutyric acid and poly-2,3-diamino propionic acid, polyethylene imine, polyallyl amine, copolymer compounds of allyl amine and diallyl amine, basic polymers such as polydiallyl amine and polyvinyl amine, or basic antibiotics such as polymyxin, streptomycin, amikacin and kanamycin, can be used.

As amino group-containing molecule, polylysine can be used preferably, and in addition, polyethylene imine and polyallyl amine can also be used preferably. In particular, epsilon-polylysine can be used preferably, as it can be prepared in large amounts by microorganism fermentation.

Epsilon-polylysine is a linear polymer in which L-lysines are linked via an amide bond between a carboxyl at the α-position and an amino group at the ϵ-position. Epsilon-polylysine can be prepared by fermentation, and for instance, a method is known, whereby a microbe that produces epsilon-polylysine (for instance, bacteria of the *Streptomyces* genus) is cultured in a liquid culture medium, and epsilon-polylysine produced and accumulated in the solution is collected (for instance, see Japanese Patent Publication No. S59-20359 and the like). The degree of polymerization (n) of epsilon-polylysine is preferably approximately 2 to 50, more preferably approximately from 20 to 40, and particularly preferably approximately from 25 to 35. Such epsilon-polylysines are also available commercially. In addition, epsilon-polylysine can also be prepared by chemical synthesis, for instance, by condensing a lysine having the protected amino group at the α position, and then eliminating the protecting group.

The substance used when partially modifying amino groups present within a molecule of an amino group-containing molecule with a molecule that is capable of reacting with an amino group is not limited in particular, as long as it is a molecule that is capable of reacting with an amino group. A molecule that is capable of forming an amine bond or an amide bond with an amino group is preferred as the molecule that is capable of reacting with an amino group, as it allows an amino group to be modified by forming an amine bond or an amide bond with the amino group. As molecules that is capable of forming an amine bond or an amide bond with an amino group, for instance, carboxylic acids (carboxyl-containing substances), aldehydes (aldehyde-containing substances), epoxy compounds (epoxy-containing substances), halogenated alkyl, and the like, can be used, among which carboxylic acids, epoxy compounds and aldehydes can be used preferably. In particular, anhydrous carboxylic acids and epoxy compounds can be used preferably as they react readily with amino groups.

As anhydrous carboxylic acids, for instance, acetic anhydride, anhydrous propionic acid, anhydrous butyric acid, phthalic anhydride, benzoic acid anhydride, maleic anhydride, anhydrous isobutyric acid, succinic anhydride, anhydrous glutaric acid, aconitic acid anhydride, citraconic acid anhydride, and the like, can be used, and acetic anhydride, anhydrous propionic acid, anhydrous butyric acid, anhydrous benzoic acid, maleic anhydride, anhydrous isobutyric acid, and the like, are preferred, and furthermore, acetic anhydride is preferred. As epoxy compounds (epoxy-containing substances), for instance, butylglycidyl ether, phenylglycidyl ether, allylglycidyl ether, 1,2-epoxy butane, 3-(2-biphenylyloxy)-1,2-epoxy propane, 1,4-butanedioldiglycidyl ether, chloromethyl oxirane, 1,2-epoxy ethyl benzene, 2,3-epoxy-1-propanol, propylene oxide, 1,2-epoxy octane, polyethyleneglycol glycidyl ether, ethylene glycoldiglycidyl ether, and the like, can be used, and butylglycidyl ether, phenylglycidyl ether are preferred, furthermore, butylglycidyl ether is preferred. As aldehydes, for instance, acetaldehyde, butyl aldehyde, isobutyl aldehyde, heptyl aldehyde, benzaldehyde and derivatives thereof, saccharides greater than disaccharides and having a reduced extremity, monosaccharides, and the like, can be used.

Among the molecules that are capable of reacting with an amino group, epoxy compounds and anhydrous carboxylic acids are preferred, furthermore, epoxy compounds are preferred, butylglycidyl ether and phenylglycidyl ether are particularly preferred, and butylglycidyl ether is especially preferred.

Modification of amino groups present within a molecule of an amino group-containing molecule can be carried out by well-known methods, or by methods conforming thereto. For instance, when modifying using epoxy compounds such as glycidyl ether, the modification can be carried out by dissolving or suspending an amino group-containing molecule in water, a polar solvent (for instance, dioxane, THF, DMF, DMSO or the like) or a mixed solution thereof, and reacting by adding thereto an epoxy compound. The amount of epoxy compound used is in general from approximately 0.1 to approximately 30-fold amount with respect to the number of moles of primary amino groups of the amino group-containing molecule contained in the carrier, and preferably from approximately 0.5 to approximately 25-fold amount. The reaction temperature is in general from 10° C. to 80° C., and preferably from 35° C. to 45° C. The reaction time is in general from approximately 10 minutes to approximately 24 hours, and preferably from approximately 2 hours to approximately 5 hours. These reaction conditions can be set suitably according to the desired ratio of modification and the like. In addition, when modifying using an anhydrous carboxylic acid such as acetic anhydride, the modification can be carried out by dissolving or suspending an amino group-containing molecule in water, polar solvent (for instance, dioxane, THF, DMF, DMSO or the like) or mixed solution thereof, and reacting by adding thereto an anhydrous carboxylic acid in the presence of a base (for instance, triethyl amine, pyridine, sodium hydroxide, potassium hydroxide or the like). The amount of anhydrous carboxylic acid used is in general from approximately 0.1 to approximately 30-fold amount with respect to the number of moles of primary amino groups of the amino group-containing molecule contained in the carrier, and preferably from approximately 0.3 to approximately 25-fold amount. The reaction temperature is in general from 10° C. to 80° C., and preferably from approximately 35° C. to approximately 45° C. The reaction time is in general from approximately 10 minutes to approximately 24 hours, and preferably from approximately 2 hours to approximately 5 hours. These reaction conditions can be set suitably according to the desired ratio of modification and the like.

The ratio of modification of the intramolecular amino groups of the amino group-containing molecule is preferably from approximately 10% to approximately 70%, more preferably from approximately 20% to approximately 60%, and particularly preferably from approximately 50% to approximately 60%. If the ratio of modification is low, there is the tendency that adsorption of highly acidic substances such as heparin cannot be suppressed sufficiently. As the ratio of modification becomes higher, although the ratio of adsorption of highly acidic substances such as heparin decreases, the ratio of adsorption of endotoxin also decreases, and there is the tendency that the endotoxin cannot be adsorbed and removed sufficiently. Such highly acidic substances are those that have a sulfate ester, a phosphoester, a carboxyl, and the like, within the molecule, and are negatively charged in the pH region of weak acid to alkali. As highly acidic substances, for instance, glycosaminoglycans and mucopolysaccharides, such as, heparin, heparan sulfate, hyaluronic acid, chondroitin sulfate, dermatan sulfate and keratan sulfate, or polyuronic acids, such as, alginic acid and pectin, or sulfated polysaccharides, such as, sulfated cellulose, sulfated chitin and sulfated chitosan, phosphorylated polysaccharides, such as, phosphorylated starch, phosphorylated mannan and phosphorylated galactan, deoxyribonucleic acid (DNA), colominic acid, polyglutamic acid, and the like, may be included.

The ratio of modification of amino groups present within a molecule of an amino group-containing molecule can be calculated from the following formula by measuring the primary amino groups present within the molecule prior to and after modification.

Ratio of modification of amino groups (%)=[(amount of primary amino groups prior to modification−amount of primary amino groups after modification)/amount of primary amino groups prior to modification]×100

Measurement of primary amino groups can be carried out by well-known methods, for instance, by the ninhydrin method. More specifically, the amount of primary amino groups can be measured, for instance, using a ninhydrin test solution for automated amino acid analyzer and 2-amino ethanol as a standard solution. Ninhydrin test solution for automated amino acid analyzer and 2-amino ethanol are commercially available (for instance, ninhydrin test solution manufactured by Wako Pure Chemical Industries, Ltd. and 2-amino ethanol manufactured by Tokyo Chemical Industry Co., Ltd., and the like). Quantitative measurement of primary amino group by the ninhydrin method can be carried out according to methods described in Kiso Seikagaku Jikken Koza (Fundamentals of Biochemical Experimental Methods), Volume 5, Kagaku-teki Sokutei (Chemical Measurements), p. 175 (Maruzen Co., Ltd.).

Endotoxin selectivity (ratio of adsorption of endotoxin/ratio of adsorption of heparin) by the endotoxin adsorbent of the present invention is preferably approximately 2 or greater, more preferably approximately 5 or greater, particularly preferably approximately 8 or greater, and most preferably approximately 10 or greater. Measurement of selectivity for endotoxin is carried out, in general, at an initial value for endotoxin of approximately 10 to approximately 1,000 EU/ml and an initial value for heparin of approximately 50 to approximately 5001 U/ml, and preferably at an initial value for endotoxin of 30 to 100 EU/ml and an initial value for heparin of 100 to 120 IU/ml.

The ratio of adsorption of endotoxin can be calculated from the following formula by measuring the endotoxin concentration in the endotoxin-containing solution prior to adsorption by the endotoxin adsorbent, and the endotoxin concentration after adsorption.

Ratio of adsorption of endotoxin $(ET)$ (%)=[(concentration of $ET$ prior to adsorption−concentration of $ET$ after adsorption)/concentration of $ET$ prior to adsorption]×100

Measurement of endotoxin can be carried out by well-known methods, for instance, by measuring the endotoxin concentration by the kinetic colorimetric method. More specifically, for instance, measurement is possible by the kinetic colorimetric method using a lysate reagent and an endotoxin standard. The lysate reagent and the endotoxin standard are commercially available (for instance, manufactured by Seikagaku Corporation, and the like). The kinetic colorimetric method can be carried out according to the methods described in, for instance, $14^{th}$ Revision of Pharmacopoeia of Japan: Endotoxin Assay, and the like.

The ratio of adsorption of heparin can be calculated from the following formula by measuring the heparin concentration prior to adsorption by the endotoxin adsorbent, and the heparin concentration after adsorption.

Ratio of adsorption of heparin $(Hep)$(%)=[(concentration of $Hep$ prior to adsorption−concentration of $Hep$ after adsorption)/concentration of $Hep$ prior to adsorption]×100

Measurement of heparin can be carried out by well-known methods, for instance, by measuring the heparin concentration by the carbazole-sulfuric acid method. More specifically, for instance, the concentration of a subject sample solution can be determined from a calibration curve created using heparin standard solutions by the carbazole-sulfuric acid method. As heparin standard solution, commercially available heparin sodium injectable, or the like, can be used (for instance, heparin sodium injectable manufactured by Mitsubishi Pharma Corporation, and the like). The carbazole-sulfuric acid method can be carried out according to methods described in, for instance, T. Bitter, H. M. Muir, Anal. Biochem., 4,330 (1962) and J. T. Galambos, Anal. Biochem., 19, 119 (1967).

The ligand of the invention may be immobilized onto a carrier, and immobilization onto a carrier is preferred on the point that the endotoxin adsorbent is readily removed after contact with the endotoxin-containing solution.

As material (carrier) used for immobilizing the ligand of the invention, common ones, such as, polysaccharides, such as, cellulose, agarose, dextran, starch, chitin and chitosan or derivatives thereof, and synthetic polymer particles (for instance, polyacrylic compounds, polystyrene compounds, polyvinyl compounds and the like) can be used. In addition, silica and glass can be used as inorganic material; however, they are not suited for alkaline treatment during removal of endotoxin within the carrier. Among these, polysaccharides can be used preferably, as the hydroxyl groups present abundantly within the molecule can be activated readily allowing immobilization of ligand to be carried readily. Cellulose, agarose, dextran, chitin, chitosan and the like can be used preferably as polysaccharides. These polysaccharides can be prepared from materials of natural origin by extraction, isolation and purification according to well-known methods, and are also commercially available. Derivatives of polysaccharides used in the invention means derivatives wherein a functional group has been introduced into polysaccharides of natural origin. As functional groups introduced into polysaccharides, for instance, optionally substituted alkyl (for instance, methyl, ethyl, butyl and the like); alcohol (for instance, hydroxyethyl, hydroxypropyl and the like); ester (for instance, acetic acid, butyric acid, phosphoric acid, sulfuric acid and the like); ion-exchange group (aminoethyl, diethyl aminoethyl, quaternary ammonium, carboxymethyl and sulfone), and the like, may be included. Derivatives of polysaccharides are not limited in particular as long as they do not impede immobilization of the ligand of the invention and, for instance, methylated polysaccharide, ethylated polysaccharide, hydroxyethylated polysaccharide, hydroxypropyl polysaccharide, and the like, may be included. More specifically, as cellulose derivatives used in the invention, for instance, hydroxypropyl cellulose, aminoethyl cellulose, and the like, may be included. As agarose derivatives, for instance, chloromethyl oxirane cross-linked agarose, agarose-acrylic co-polymerization product, and the like, may be included. As dextran derivatives, for instance, chloromethyl oxirane cross-linked dextran, hydroxypropylated dextran, and the like, may be included. As chitin derivatives, for instance, chloromethyl oxirane cross-linked chitin, and the like, may be included. As chitosan derivative, for instance, chloromethyl oxirane cross-linked chitosan, and the like, may be included. Such derivatives of polysaccharides can be prepared by well-known methods, or by methods conforming thereto, and are also commercially available.

In addition, as shapes of the carrier used in the invention, shapes generally used as base materials for separation, such as, spherical (for instance, spherical particle and the like), particular, fibrous, granular, monolith column, hollow fiber, membranous (for instance, flat membrane and the like) can be used, and spherical, membranous, granular, fibrous and the like are preferable. Spherical particles can be used particularly preferably, as the volume used can be set suitably when using in column method or batch method. The particle size of the spherical particles is in general from approximately 1 to approximately 1,000 μm, and is selected suitably according to the purpose of use and the like. For instance, when using in the column method, the particle size is preferably from approximately 50 to approximately 500 μm. When using in the batch method, the particle size is preferably from approximately 10 to approximately 300 μm. As spherical particles, spherical cellulose, spherical sepharose, spherical agarose, spherical dextran, spherical chitosan and cross-linked spherical particles thereof, spherical silica, styrene beads, acrylic beads, and the like can be used preferably. Such spherical particles are commercially available and, for instance, *Cellufine (manufactured by Chisso Corporation), sepharose, Sephadex (manufactured by Amersham Biosciences), Viscopearl (manufactured by Rengo Co., Ltd.), Perloza MT series (manufactured by Iontsorb), "Cellulose, Beaded" (catalogue code: C8204)* (manufactured by Sigma), Toyopearl (manufactured by Tosoh Corporation), and the like, can be used.

Among the carriers used in the invention, spherical cellulose, spherical sepharose, spherical dextran and the like can be used preferably.

Immobilization of the ligand of the invention can be carried out by well-known methods, or by methods conforming thereto. As ligand immobilization methods, general methods described in references such as, for instance, Jikken to Oyo (Experiment and Application): Affinity Chromatography, Ichiro Chibata, Tetsuya Tosa, Yushi Matsuo, Kodansha Scientific, and Immobilized Affinity Ligand Techniques, G. T. Hermanson, A. K. Mallia, P. K. Smith ACADEMIC PRESS, INC., can be used. In particular, the method for immobilizing an amino group-containing ligand by the epoxy activation method can be used preferably in the invention in order not to lose the basic character of amino groups.

Immobilization of ligand by the epoxy activation method can be carried out, for instance, by adding water and an NaOH solution to a carrier (for instance, spherical cellulose or the like) and stirring, then adding an epoxy activator (for instance, epichlorohydrin or the like) for reaction to prepare an epoxy-activated carrier (for instance, epoxy-activated cellulose particle or the like), and adding an amino group-containing molecule (for instance, epsilon-polylysine or the like) to the obtained epoxy-activated carrier for reaction.

As methods for modifying amino groups within the ligand immobilized onto the carrier of the invention, the method whereby an unmodified ligand (that is to say, an amino group-containing molecule with no modified amino groups) is first immobilized onto a carrier and then modified, or, the method whereby amino groups within a ligand are modified, then the modified ligand is immobilized onto a carrier, are possible. Among these, the method whereby an unmodified ligand is immobilized onto a carrier and then modified is preferred in the invention, as washing and recovering the products become easy.

Consequently, the endotoxin adsorbent of the invention, that is to say, the endotoxin adsorbent, which is an immobilized ligand wherein amino groups have been partially modified, can be prepared readily by immobilizing an unmodified ligand onto a carrier, and then reacting with a molecule that is capable of reacting with an amino group, such as, anhydrous carboxylic acid, epoxy compound, and the like.

An endotoxin adsorbent, wherein a ligand, which is a polylysine wherein amino groups have been partially modified by a molecule that is capable of forming an amino bond or an amide bond with an amino group, is immobilized onto a carrier, can be prepared, for instance, by immobilizing a polylysine with unmodified amino groups onto a carrier, then reacting amino groups of the polylysine with a molecule that is capable of forming an amino bond or an amide bond with an amino group.

Although partial modification of amino groups may be carried out by modifying the amino groups, then partially removing modified groups from the modified amino groups, it is preferable to modify the amino groups partially, and not carry out removal of modified groups.

2. Method for Adsorbing and Removing Endotoxin

The second embodiment of the invention relates to a method for adsorbing and removing endotoxin by bringing the endotoxin adsorbent of the invention in contact with an endotoxin-containing solution.

Since the endotoxin adsorbent of the invention adsorbs endotoxin effectively, endotoxin can be removed from an endotoxin-containing solution by bringing the endotoxin adsorbent in contact with the endotoxin-containing solution to adsorb endotoxin with the endotoxin adsorbent.

There is no particular limitation on the endotoxin-containing solution that the method of the invention is to adsorb and remove the endotoxin from. For instance, endotoxin can be adsorbed and removed by the method of the invention from endotoxin-containing medicinal drug products, blood and the like. As the endotoxin adsorbent of the invention allows endotoxin to be selectively adsorbed and removed even when a highly acidic substance such as heparin co-exists, the method of the invention is effective in particular when removing endotoxin from endotoxin-containing solutions such as medicinal drug product, blood, blood plasma component, which contain heparin.

As endotoxin-containing solutions containing a highly acidic substance, for instance, medicinal drug products containing heparin, such as, heparin sodium solution, or heparin solution, blood or blood plasma component, and the like, used in the preparation process thereof, may be included. Blood or blood plasma component may be that derived from a patient administered with a highly acidic substance such as heparin, in addition, may also be blood or blood plasma component to which a highly acidic substance such as heparin has been added.

There is no limitation on the method for adsorbing and removing endotoxin by bringing into contact an endotoxin adsorbent and an endotoxin-containing solution, and methods generally used in relevant technical fields can be used; for instance, the column method, the batch method, and the like, are used. The column method and the batch method can be carried out according to methods generally used in relevant technical fields. For instance, in the case of the column method, a column is filled with the endotoxin adsorbent of the invention, after washing with a buffer solution, saline or the like, a solution such as medicinal drug product or blood, which contain endotoxin, is run through to adsorb endotoxin within the solution with the endotoxin adsorbent, and a solution from which endotoxin has been removed is obtained as a flow-through fraction. In addition, in the case of the batch method, an endotoxin-containing solution is added to the endotoxin adsorbent of the invention, after stirring to adsorb the endotoxin to the endotoxin adsorbent, the endotoxin adsorbent is separated and removed from the solution by filtration, centrifugal separation or the like, to allow a solution from which endotoxin has been removed to be obtained.

As the endotoxin adsorbent of the invention allows endotoxin to be selectively adsorbed and removed even when a highly acidic substance such as heparin co-exists, it can be used particularly suitably in extracorporeal circulation therapy, in which, for instance, prior to returning into the body of the patient blood or blood plasma component that has been taken out from the body of a patient, the endotoxin in the blood or the blood plasma component is removed using the endotoxin adsorbent of the invention (for instance, using a column filled with the endotoxin adsorbent of the invention), and the blood or blood the plasma component from which endotoxin has been removed is returned into the body of the patient. In addition, the method of the invention can also be used suitably in cases where a patient is receiving heparin administration, or in cases where heparin is added to blood or blood plasma component taken out from the body of a patient to suppress blood coagulation.

EXAMPLES

Hereinafter the invention will be described with examples and comparative examples; however, the invention is not limited to these examples.

Comparative Example 1

Immobilization of Unmodified Ligand onto Carrier (Adsorbent A)

To 100 g of Cellufine (wet weight; moisture content: 91.7%), which is a spherical cellulose prepared according to the methods described in Japanese Patent Publication No. S63-62252, 78 ml of pure water and 64 g of 20% (weight) NaOH solution were added, and this was stirred for 1 hour while maintained at 30° C. Next, 38 g of epichlorohydrin was added and reacted by stirring for 2 hours. The reaction mixed-solution was filtered after the reaction end, and gels were recovered. The gel repeated washing with water and filtered until filtrate became neutrality The total amount of epoxy-activated cellulose particle obtained in this way was reacted by adding 90 ml of pure water, 30 ml of 25% epsilon-poly-L-lysine solution (manufactured by Chisso Corporation; average molecular weight: 4,700) and stirring this for 2 hours at 45° C. After completion of the reaction, the product was washed to obtain an endotoxin adsorbent (adsorbent A).

The amount of epsilon-poly-L-lysine introduced was determined by the following calculation by measurement of the total nitrogen content (TN amount). Note that the sample for the total nitrogen content (TN amount) measurement was measured by the Kehldahl method, using a sample that was rinsed and subsequently dried at 80° C.

epsilon-poly-$L$-lysine amount (mg/g-dry)=($Lys$–$H_2O$)×($TN$ amount÷2×$N$)±1000

Herein, Lys–$H_2O$ is the value of a molecular weight of lysine molecule subtracted with a molecular weight of water molecule, 128.17. N represents the atomic weight of nitrogen. Further, mg/g-dry represents the amount of polylysine (mg) per gram of dried sample.

As a result, the polylysine content of Comparative Example 1 was 140 mg/g-dry.

Comparative Example 2

Immobilization of Unmodified Ligand onto Carrier (Adsorbent B)

To 100 g of Cellufine (wet weight; moisture content: 91.7%), which is spherical cellulose prepared according to the methods described in Japanese Patent Publication No. S63-62252, 163 ml of pure water and 49 g of 20% (weight) NaOH solution were added, and this was stirred for 1 hour while maintained at 30° C. Next, 47 g of epichlorohydrin was added and reacted by stirring for 2 hours. The reaction mixed-solution was filtered after the reaction end, and gels were recovered. The gel repeated washing with water and filtered until filtrate became neutrality. The whole amount of epoxy-activated cellulose particle obtained in this way was reacted by adding 90 ml of pure water, 30 ml of 25% epsilon-poly-L-lysine solution (manufactured by Chisso Corporation; average molecular weight: 4,700) and stirring this for 2 hours at 45° C. After completion of the reaction, the product was washed to obtain an endotoxin adsorbent (adsorbent B).

The polylysine content of Comparative Example 2 was 94 mg/g-dry.

Example 1

Modification of Amino Groups of Adsorbent a by Butylglycidyl Ether

Amino groups of endotoxin adsorbent (adsorbent A) obtained in Comparative Example 1 were modified by butylglycidyl ether.

To 100 g of adsorbent A (wet weight; moisture content: 89%) 150 ml of pure water was added. An amount of 11.5 g of butylglycidyl ether was added and reacted for 4 hours at 35° C. to 40° C. After the reaction, the product was washed 5 times with methanol and 5 times with pure water to obtain the endotoxin adsorbent (ABu-1) of Example 1.

Example 2 to 14

Modification of Amino Groups of Adsorbent B by Glycidyl Ethers

Next, with the adsorbent B obtained in Comparative Example 2 as the starting material, amino groups of epsilon-poly-L-lysine, which is an immobilized ligand, were modified by glycidyl ethers.

In the cases of Examples 2 to 12, 40 ml of pure water was added to 30 g of adsorbentB(wet weight; moisture content: 89.5%). In the cases of Examples 13 and 14, 40 ml of dioxane was used instead of 40 ml of pure water. Glycidyl ethers shown in Table 1 were added to a suspension of adsorbent and reacted for 4 hours at 35° C. to 40° C. After the reaction, the product was washed 5 times with methanol and 5 times with pure water.

Glycidyl ethers used in Examples 2 to 14 and the amounts thereof fed are shown in Table 1.

TABLE 1

Charged amounts of glycidyl ethers

| Example No. (adsorbent name) | Name of glycidyl ethers | Charged amount (g) |
|---|---|---|
| Example 2 (BPh-1) | Phenylglycidyl ether | 0.16 |
| Example 3 (BPh-2) | Phenylglycidyl ether | 0.34 |
| Example 4 (BPh-3) | Phenylglycidyl ether | 0.66 |
| Example 5 (BPh-4) | Phenylglycidyl ether | 0.94 |
| Example 6 (BPh-5) | Phenylglycidyl ether | 1.90 |
| Example 7 (BPh-6) | Phenylglycidyl ether | 3.77 |
| Example 8 (BBu-1) | Butylglycidyl ether | 1.71 |
| Example 9 (BBu-2) | Butylglycidyl ether | 3.21 |
| Example 10 (BBu-3) | Butylglycidyl ether | 6.40 |
| Example 11 (BPEG8-1) | DENACOL EX-830 (polyethylene glycol diglycidyl ether) | 4.26 |
| Example 12 (BPEG8-2) | DENACOL EX-830 (polyethylene glycol diglycidyl ether) | 8.52 |
| Example 13 (BPEG21-1) | DENACOL EX-861 (polyethylene glycol diglycidyl ether) | 9.34 |
| Example 14 (BPEG21-2) | DENACOL EX-861 (polyethylene glycol diglycidyl ether) | 18.68 |

Cas No. 122-60-1 (manufactured by Kishida Chemical Co., Ltd.) was used for phenylglycidyl ether, Cas No. 2426-08-6 (manufactured by Wako Pure Chemical Industries, Ltd.) was used for butylglycidyl ether, and DENACOL EX-830 and DENACOL EX-861 manufactured by Nagase ChemteX Corporation were used for polyethyleneglycol diglycidyl ether.

Examples 15 to 21

Modification of Amino Groups of Adsorbent B by Acetic Anhydride

With the adsorbent B obtained in Comparative Example 2 as the starting material, amino groups of epsilon-poly-L-lysine, which is an immobilized ligand, were modified by acetic anhydride.

To 30 g of adsorbent B (wet weight; moisture content: 89.5%), 40 ml of pure water was added. To a suspension of adsorbent B, triethyl amine and acetic anhydride shown in Table 2 were added and reacted for 4 hours at 35° C. to 40° C. After the reaction, the product was washed 3 times with pure water, then 3 times with 0.2 N sodium hydroxide solution, and further washed with pure water until the washing solution became neutral.

The amounts of triethyl amine and acetic anhydride fed in Example 15 to 21 are shown in Table 2.

TABLE 2

Charged amounts of triethyl amine and acetic anhydride fed

| Example No. (adsorbent name) | Triethyl amine (g) | Acetic anhydride (g) |
|---|---|---|
| Example 15 (BAc-1) | 2.6 | 1.32 |
| Example 16 (BAc-2) | 5.2 | 2.63 |
| Example 17 (BAc-3) | 10.5 | 5.27 |
| Example 18 (BAc-4) | 0.12 | 0.06 |
| Example 19 (BAc-5) | 0.24 | 0.12 |
| Example 20 (BAc-6) | 0.44 | 0.22 |
| Example 21 (BAc-7) | 0.88 | 0.44 |

Test Example 1

Measurement of Ratio of Modification of Amino Groups within Ligand

The ratio of modification of amino groups within a ligand was calculated with the following calculation formula from the value determined by the ninhydrin method. As the ninhydrin reaction occurs with respect to primary amino groups, the extent of modification of amino groups is known by measuring the amino groups prior to and after modification using the ninhydrin method.

1 ml of ion-exchanged water containing 0.004 g of dried adsorbent was put into a test tube with a screw cap. 1 ml of ninhydrin test solution (manufactured by Wako Pure Chemical Industries, Ltd.) was added into the test tube and the tube was heated in boiling water for 20 minutes. After cooling with tap water, 8 ml of ethyl cellosolve (manufactured by Wako Pure Chemical Industries, Ltd.) was added and mixed thoroughly. The absorption of the supernatant at 570 nm was measured. 2-amino ethanol (manufactured by Tokyo Chemical Industry Co., Ltd.) was used as standard for amino group.

Ratio of modification of amino groups (%)=[(amount of primary amino groups prior to modification−amount of primary amino groups after modification)/amount of primary amino groups prior to modification]×100

The ratios of modification of amino groups within the respective ligands for the endotoxin adsorbents of Examples 1 to 21 are shown in Table 3.

TABLE 3

Ratio of modification of amino groups within ligand

| Example No. (adsorbent name) | Ratio of modification of amino groups (%) |
|---|---|
| Example 1 (ABu-1) | 55 |
| Example 2 (BPh-1) | 25 |
| Example 3 (BPh-2) | 19 |
| Example 4 (BPh-3) | 37 |
| Example 5 (BPh-4) | 46 |
| Example 6 (BPh-5) | 38 |
| Example 7 (BPh-6) | 57 |
| Example 8 (BBu-1) | 57 |
| Example 9 (BBu-2) | 54 |
| Example 10 (BBu-3) | 3 |
| Example 11 (BPEG8-1) | 50 |
| Example 12 (BPEG8-2) | 62 |
| Example 13 (BPEG21-1) | 31 |
| Example 14 (BPEG21-2) | 49 |
| Example 15 (BAc-1) | 92 |
| Example 16 (BAc-2) | 92 |
| Example 17 (BAc-3) | 92 |
| Example 18 (BAc-4) | 38 |
| Example 19 (BAc-5) | 58 |
| Example 20 (BAc-6) | 80 |
| Example 21 (BAc-7) | 89 |

The primary amino group content for adsorbent A was 820 μmol/g (dry weight). The primary amino group content for adsorbent B was 680 μmol/g (dry weight).

Test Example 2

Measurement of Endotoxin Removal Capability in the Presence of Heparin

Adsorbent B and endotoxin adsorbents of Examples 2 to 14 and 18 to 21 were immersed in 0.2N sodium hydroxide solution for 18 hours or longer, and then washed with injectable distilled water until the solution became neutral, to make them endotoxin-free.

0.7 g (wet weight) of each endotoxin-free adsorbent was put into a dry heat sterilized Erlenmeyer flask. 10 ml of test solution with the composition shown in the table below was added into the flask, and the flask was shaken at 30° C. for 2 hours. Thereafter, the amount of endotoxin and the amount of heparin in the supernatant were measured (Table 4).

TABLE 4

Ability to remove endotoxin from solution where heparin co-exists

| Comparative Example/ Example No. (adsorbent name) | Initial endotoxin level EU/ml | Initial heparin level IU/ml | Ratio of adsorption of endotoxin (%) | Ratio of adsorption of heparin (%) | Endotoxin/ heparin |
|---|---|---|---|---|---|
| Comparative Example 2 (adsorbent B) | 46.5 | 103 | 85.6 | 59 | 1.5 |
| Example 2 (BPh-1) | 47.3 | 104 | 99.1 | 56 | 1.8 |
| Example 3 (BPh-2) | 47.3 | 104 | 99.4 | 46 | 2.2 |

TABLE 4-continued

Ability to remove endotoxin from solution where heparin co-exists

| Comparative Example/<br>Example No.<br>(adsorbent name) | Initial<br>endotoxin<br>level<br>EU/ml | Initial<br>heparin<br>level<br>IU/ml | Ratio of<br>adsorption<br>of endotoxin<br>(%) | Ratio of<br>adsorption<br>of heparin<br>(%) | Endotoxin/<br>heparin |
|---|---|---|---|---|---|
| Example 4 (BPh-3) | 47.3 | 104 | 99.6 | 35 | 2.8 |
| Example 5 (BPh-4) | 47.3 | 103 | 99.8 | 43 | 2.3 |
| Example 6 (BPh-5) | 47.3 | 103 | 99.9 | 41 | 2.4 |
| Example 7 (BPh-6) | 47.3 | 103 | 99.9 | 29 | 3.4 |
| Example 8 (BBu-1) | 36.2 | 103 | 99.3 | 12 | 8.3 |
| Example 9 (BBu-2) | 36.2 | 103 | 99.0 | 9 | 11.0 |
| Example 10 (BBu-3) | 36.2 | 103 | 94.5 | 63 | 1.5 |
| Example 11 (BPEG8-1) | 49.6 | 103 | 48 | 8 | 6.0 |
| Example 12 (BPEG8-2) | 49.6 | 103 | 22 | 8 | 2.8 |
| Example 13 (BPEG21-1) | 49.6 | 103 | 47 | 9 | 5.2 |
| Example 14 (BPEG21-2) | 49.6 | 103 | 7 | 2 | 3.5 |
| Example 18 (BAc-4) | 94.5 | 119 | 76.0 | 41 | 1.9 |
| Example 19 (BAc-5) | 94.5 | 119 | 27.4 | 11 | 2.5 |
| Example 20 (BAc-6) | 94.5 | 119 | 41.4 | 9 | 4.6 |
| Example 21 (BAc-7) | 94.5 | 119 | 60.8 | 2 | 30.4 |

LPS (*E. coli* 0110: B4, manufactured by Sigma) was used for endotoxin and heparin sodium injectable (manufactured by Mitsubishi Pharma Corporation) was used for heparin.

It became clear that, by modifying amino groups, the value endotoxin/heparin, which represents selectivity for endotoxin, became greater than Comparative Example 2 (adsorbent B).

[Method for Measuring Endotoxin]

The endotoxin concentration was measured using a lysate reagent (manufactured by Seikagaku Corporation) and an endotoxin standard (manufactured by Seikagaku Corporation) by the kinetic colorimetric method (14$^{th}$ Revision of Pharmacopoeia of Japan: Endotoxin Assay).

Method for Quantifying Heparin

Quantification of heparin was carried out by measuring the heparin concentration of each subject sample solution and each standard solution for calibration curve by the carbazole-sulfuric acid method, with commercial 1,000 IU/ml heparin sodium injectable serving as the standard stock solution.

The 1,000 IU/ml heparin sodium injectable diluted with physiological saline to prepare 50 IU/ml and 25 IU/ml solutions, and physiological saline serving as 0 IU/ml, were used as standard solutions. Each subject sample solution was diluted two-fold with physiological saline. 2.5 ml of sodium borate in sulfuric acid solution (9.5 mg/ml concentrated sulfuric acid solution) was put into a test tube with a screw cap and the tube was cooled on ice for approximately 20 minutes, then 0.5 ml of sample solution was put into the tube and the solution was mixed by stirring. After boiling for 10 minutes in boiling water, the tube was cooled on ice, then 0.1 ml of carbazole solution (1.25 mg/ml ethanol solution) was added into the tube and the solution was mixed by stirring. Then, after boiling for 15 minutes and cooled with water, absorption was measured at 530 nm to quantify heparin.

Test Example 3

Measurement of Endotoxin Removal Capability in an Endotoxin, BSA and Heparin Co-Existing System The endotoxin adsorbents from Comparative Example 1 (adsorbent A), Example 1 (ABu-1) and Example 9 (BBu-2) were compared for their endotoxin removal capabilities in an endotoxin, bovine serum albumin (BSA) and heparin co-existing system.

LPS (*E. coli* 0110: B4, manufactured by Sigma) was used for endotoxin, heparin sodium injectable (manufactured by Mitsubishi Pharma Corporation) was used for heparin, and albumin, bovine serum derived (manufactured by Wako Pure Chemical Industries, Ltd.) was used for bovine serum albumin.

The adsorbents were immersed in 0.2 N sodium hydroxide solution for 18 hours or longer, then washed with injectable distilled water until it became neutral to make it endotoxin-free.

0.7 g (wet weight) of each endotoxin-free adsorbent was put into a dry heat sterilized Erlenmeyer flask. 10 ml of test solution with the composition shown in the table below was added into the flask, and the flask was shaken at 30° C. for 2 hours. Thereafter, the amount of endotoxin, the amount of heparin, and the amount of BSA in the supernatant were measured (Table 5).

TABLE 5

Comparison of abilities of endotoxin adsorbents from Comparative Example 1, Example 1 and Example 9 to adsorb endotoxin from BSA-LPS mixed solution

| Comparative<br>Example/<br>Example No.<br>(adsorbent name) | ET<br>initial<br>level<br>EU/ml | Hep<br>initial<br>level<br>IU/ml | BSA<br>initial<br>level<br>mg/ml | Ratio of<br>adsorption<br>of ET<br>% | Ratio of<br>adsorption<br>of Hep<br>% | Ratio of<br>adsorption<br>of BSA<br>% |
|---|---|---|---|---|---|---|
| Comparative Example 1 | 51 | 104 | 1.0 | 55 | 83 | 27 |
| (adsorbent A) | 51 | 104 | 1.0 | 53 | 81 | 28 |
| Example 1 | 51 | 104 | 1.0 | 76 | 30 | 16 |
| (ABu-1) | 51 | 104 | 1.0 | 76 | 34 | 18 |

TABLE 5-continued

Comparison of abilities of endotoxin adsorbents from Comparative Example 1,
Example 1 and Example 9 to adsorb endotoxin from BSA-LPS mixed solution

| Comparative Example/ Example No. (adsorbent name) | ET initial level EU/ml | Hep initial level IU/ml | BSA initial level mg/ml | Ratio of adsorption of ET % | Ratio of adsorption of Hep % | Ratio of adsorption of BSA % |
|---|---|---|---|---|---|---|
| Example 9 | 51 | 104 | 1.0 | 78 | 41 | 28 |
| (BBu-2) | 51 | 104 | 1.0 | 78 | 31 | 29 |

In Table 5, ET represents endotoxin, Hep represents heparin and BSA represents bovine serum albumin.

[Method for Quantifying BSA]

Quantification of BSA was carried out by measuring the absorption at 280 nm.

Test Example 4

Removal of endotoxin from heparin co-existing solution by the column method

A column was filled with 5 ml of endotoxin adsorbent of Example 1 (ABu-1), left in contact with 0.2 N sodium hydroxide solution for 18 hours and then washed with injectable distilled water until it became neutral to make it endotoxin-free. 25 ml of buffer solution described below was run through the column to equilibrate.

A test solution containing heparin and endotoxin-containing test solution with the following composition was run through, and the amount of endotoxin and the amount of heparin in the column eluate were measured (Table 6).

TABLE 6

Removal of endotoxin from
heparin-containing buffer solution by the column method

| Item | |
|---|---|
| Equilibration buffer solution composition | Aqueous solution adjusted to pH 7.4 with acetic acid, containing: NaCl: 105 mmol/l; KCl: 2 mmol/l; NaHCO$_3$: 25 mmol/l; and CH$_3$COONa: 10 mmol/l. |
| Test solution | The above-mentioned equilibration buffer solution containing 50.8 EU/ml of endotoxin (LPS) and 94 IU/ml of heparin. |
| Chromatography conditions | Column: 5.6 ml; flow rate: 1 ml/min; fraction: 5.6 ml/faction. |

The result of endotoxin removal from heparin-containing buffer solution by the column method is shown in FIG. 1. In FIG. 1, [C/Co] represents the concentration of heparin or endotoxin, the concentration in the eluent is represented by [α] and the concentration in the test solution (initial value) is represented by [Co].

As shown in FIG. 1, heparin was not adsorbed much, and [C/Co] has a value close to one. On the other hand, it is clear that endotoxin was selectively adsorbed, with a [C/Co] of 0.01 or less even at fraction 30.

INDUSTRIAL APPLICABILITY

As the endotoxin adsorbent of the invention makes endotoxin to be adsorbed and removed selectively from a solution containing a highly acidic substance such as heparin, it is useful as base material for medical therapy, adsorbent or filler for chromatography, or the like, for removing endotoxin from solutions where highly acidic polysaccharides, such as heparin, and the like, co-exist.

The invention claimed is:

1. An endotoxin adsorbent comprising a ligand,
   wherein said ligand binds to the endotoxin and comprises a polylysine,
   wherein said endotoxin adsorbent is prepared by immobilizing an unmodified ligand polylysine onto a carrier and then reacting at least one amino group present within said polylysine, which is other than an amino group used for binding said polylysine to carrier, with an ether selected from the group consisting of butylglycidyl ether and phenylglycidyl ether, so that said ether forms an amine bond with intramolecular amino groups of said polylysine other than an amino group used for bonding said ligand to said carrier,
   wherein the shape of said carrier is at least one selected from the group of spherical, membranous, granular or fibrous.

2. The endotoxin adsorbent according to claim 1, wherein said carrier is at least one polysaccharide or derivative thereof.

3. The endotoxin adsorbent according to claim 2, wherein said at least one polysaccharide is at least one of cellulose, agarose, dextran, chitin or chitosan.

4. The endotoxin adsorbent according to claim 1, wherein said carrier is at least one of spherical cellulose, spherical sepharose or spherical dextran.

5. The endotoxin adsorbent according to claim 1, wherein the ratio of modification of amino groups of said polylysine is from approximately 20 to approximately 60%.

6. The endotoxin adsorbent according to claim 1, wherein said polylysine is epsilon-polylysine.

7. A method for adsorbing and removing endotoxin comprising bringing the endotoxin adsorbent according to claim 1 in contact with an endotoxin-containing solution.

8. A method for selectively adsorbing and removing endotoxin by bringing the endotoxin adsorbent according to claim 1 in contact with an endotoxin-containing solution containing heparin.

9. The method according to claim 7, wherein said contact of said endotoxin adsorbent with said endotoxin-containing solution is carried out using a column filled with said endotoxin adsorbent.

* * * * *